(12) United States Patent
Li et al.

(10) Patent No.: US 10,304,007 B2
(45) Date of Patent: May 28, 2019

(54) USING A PLURALITY OF HETEROGENEOUS DECISION ENGINES TO PRODUCE A SINGLE DECISION

(71) Applicant: International Business Machines Corporation, Armonk, NY (US)

(72) Inventors: Xiang Li, Beijing (CN); Haifeng Liu, Beijing (CN); Jing Mei, Beijing (CN); Guo Tong Xie, Beijing (CN); Yi Qin Yu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 696 days.

(21) Appl. No.: 14/962,078

(22) Filed: Dec. 8, 2015

(65) Prior Publication Data

US 2017/0161634 A1 Jun. 8, 2017

(51) Int. Cl.
*G06N 20/00* (2019.01)
*G06N 99/00* (2019.01)
*G06F 19/00* (2018.01)
*G06N 5/04* (2006.01)

(52) U.S. Cl.
CPC ............. *G06N 20/00* (2019.01); *G06F 19/00* (2013.01); *G06N 99/005* (2013.01); *G06F 19/30* (2013.01); *G06N 5/04* (2013.01)

(58) Field of Classification Search
USPC .......................................................... 706/12
See application file for complete search history.

(56) References Cited

U.S. PATENT DOCUMENTS 7,711,623 B2 * 5/2010 Smith .................... G06Q 40/06
705/35
7,925,874 B1 * 4/2011 Zaitsev ............... G06F 9/44505
713/1
8,099,382 B2 * 1/2012 Liu .................... G06F 17/30592
707/601

(Continued)

FOREIGN PATENT DOCUMENTS

CN 103902591 A 7/2014

OTHER PUBLICATIONS

An integration profile of rule engines for clinical decision support systems, Yinsheng Zhang; Haomin Li; Huilong Duan; Qian Shang; 2016 International Conference on Progress in Informatics and Computing (PIC), Dec. 23-25, 2016, IEEE pp. 762-766.*

(Continued)

*Primary Examiner* — Michael B Holmes
(74) *Attorney, Agent, or Firm* — Grant Johnson; Otterstedt, Ellenbogen & Kammer, LLP

(57) ABSTRACT

A method for using a plurality of decision engines to produce a single decision comprises: receiving heterogeneous data from the plurality of decision engines comprising a set of class labels from each of the plurality of decision engines, wherein the set of class labels from at least a first decision engine differs from the set of class labels from at least a second decision engine; generating a single set of unified class labels from the heterogeneous data; calculating at least one value corresponding to each of at least a subset of the unified class labels; and performing decision fusion on at least the subset of the unified class labels and corresponding values to produce the single decision.

20 Claims, 3 Drawing Sheets

(56) References Cited

U.S. PATENT DOCUMENTS

| | | | | |
|---|---|---|---|---|
| 8,166,054 | B2* | 4/2012 | Fu | G06F 17/30938 |
| | | | | 707/755 |
| 8,214,314 | B2 | 7/2012 | Bonissone et al. | |
| 8,301,841 | B2* | 10/2012 | Hou | G06F 17/3048 |
| | | | | 711/118 |
| 8,341,060 | B2* | 12/2012 | Smith | G06Q 40/06 |
| | | | | 705/36 R |
| 8,341,173 | B2* | 12/2012 | Li | G06F 17/30967 |
| | | | | 707/713 |
| 8,544,058 | B2* | 9/2013 | Lim | G06F 17/3089 |
| | | | | 726/1 |
| 8,560,563 | B2* | 10/2013 | Chieu | G06F 9/5038 |
| | | | | 706/45 |
| 8,639,711 | B2* | 1/2014 | Liu | G06F 17/3051 |
| | | | | 707/760 |
| 8,700,557 | B2 | 4/2014 | Gupta et al. | |
| 8,918,415 | B2* | 12/2014 | Li | G06F 17/30967 |
| | | | | 707/713 |
| 8,990,886 | B2* | 3/2015 | Lim | G06F 17/3089 |
| | | | | 726/1 |
| 9,043,256 | B2* | 5/2015 | Pan | G06N 5/02 |
| | | | | 706/45 |
| 9,171,058 | B2* | 10/2015 | Ma | G06F 17/30604 |
| 9,253,216 | B2* | 2/2016 | Lim | G06F 17/3089 |
| 9,275,144 | B2* | 3/2016 | Pan | G06F 17/30864 |
| 9,552,389 | B2* | 1/2017 | Chieu | G06F 9/5038 |
| 9,703,978 | B2* | 7/2017 | Lim | G06F 17/3089 |
| 9,971,806 | B2* | 5/2018 | Hu | G06F 17/30469 |
| 10,068,668 | B2* | 9/2018 | Cao | G06F 19/00 |
| 2012/0023062 | A1 | 1/2012 | Vashist | |
| 2012/0287401 | A1 | 11/2012 | Bizios et al. | |

OTHER PUBLICATIONS

SAR Automatic Target Recognition Using Discriminative Graphical Models Umamahesh Srinivas; Vishal Monga; Raghu G. Raj IEEE Transactions on Aerospace and Electronic Systems Year: 2014, vol. 50, Issue: 1 pp. 591-606 IEEE Journals & Magazines.*

Knowledge Based Requirement Engineering Framework for Emergency Management System Velayutham Pavanasam; Chandrasekaran Subramaniam; Mannu Mulchandani; Aishwarya Parthasarthy 2010 Second International Conference on Computer Engineering and Applications Year: 2010, vol. 1 pp. 601-605 IEEE Conferences.*

Nonlinear process representation using ARMAX models with time dependent coefficients R. B. Mrad; J. A. Levitt Proceedings of the 37th IEEE Conference on Decision and Control (Cat. No. 98CH36171) Year: 1998, vol. 1 pp. 495-500 vol. 1 IEEE Conferences.*

Scientific World Journal Fusion of Heterogeneous Intrusion Detection Systems for Network Attack Detection Jayakumar Kaliappan, Revathi Thiagarajan, and Karpagam Sundararajan, pp. 1-8.*

Transactions on Information Forensics and Security, vol. , No. , 2009 Improvement in Intrusion Detection with Advances in Sensor Fusion Ciza Thomas and N. Balakrishnan pp. 1-10.*

Human-centric Computing and Information Sciences Design of fusion technique-based mining engine for smart business Atsushi Sato, Runhe Huang and Neil Y Yen pp. 1-16 May 13, 2015.*

Vehicle Classification on Multi-Sensor Smart Cameras Using Featureand Decision-Fusion Andreas Klausne, Allan Tengg Bernhard Rinner 2007 IEEE pp. 67-74.*

Huang & Wang, "Dynamic Combination of Multiple Classifiers Based on Normalizing Decision Space," 2010, WASE International Conference on Information Engineering (ICIE), v. 1, p. 149-153, Institute of Electrical and Electronics Engineers (IEEE).

Vizedom et al., "Knowledge Base Support for Decision Making Using Fusion Techniques in a C2 Environment," 2001, Proceedings of the Fourth International Conference on Information Fusion, pp. 1-10, International Society of Information Fusion (ISIF).

* cited by examiner

USING A PLURALITY OF HETEROGENEOUS DECISION ENGINES TO PRODUCE A SINGLE DECISION

BACKGROUND OF THE INVENTION

The present invention relates generally to the electrical, electronic and computer arts, and, more particularly, to techniques for using a plurality of heterogeneous decision engines to produce a single decision.

Improving the accuracy and performance of decision support systems (DSS) remains a persistent challenge within the fields of machine learning and pattern recognition. There are often variety of decision engines for use in DSS, such as knowledge-based and/or data-based analysis modules, which typically generate one or more labels (e.g., textual descriptions of options) and corresponding values (e.g., a numeric representation of the support degree for each option). However, these decision engines are typically imperfect classifiers with varying strengths and weaknesses. Multiple classifier systems (MCS) combine different opinions from different decision engines to make a final decision in a process known as decision fusion. Combining the outputs from different decision engines allows all decision engines to contribute to the final decision, which is of higher quality than a decision generated by any single decision engine, which as noted above are typically imperfect classifiers. MCS is sometimes referred to as ensemble learning or mixture of experts.

However, a conventional MCS often requires each of its constituent classifiers to produce uniform (e.g. homogeneous) labels. Thus, a conventional MCS typically is limited to classifiers (e.g., decision engines) which were designed and constructed specifically for use in the MCS. Legacy decision engines which were previously developed and constructed for other purposes cannot be easily integrated within conventional MCSes because these decision engines may produce output values with non-uniform (e.g. heterogeneous) labels relative to each other. For example, legacy decision engines may refer to the same concept using different terms (e.g., synonyms) and/or one of the legacy decision engines may produce output values with labels having a different granularity than another of the legacy decision engines.

BRIEF SUMMARY

Principles of the invention, in accordance with embodiments thereof, provide techniques for using a plurality of heterogeneous decision engines to produce a single decision. In one aspect, a method for using a plurality of decision engines to produce a single decision comprises receiving heterogeneous data from the plurality of decision engines comprising a set of class labels from each of the plurality of decision engines, wherein the set of class labels from at least a first decision engine differs from the set of class labels from at least a second decision engine; generating a single set of unified class labels from the heterogeneous data; calculating at least one value corresponding to each of the unified class labels; and performing decision fusion on the unified class labels and corresponding values to produce the single decision.

In accordance with another embodiment of the invention, an apparatus includes a memory and at least one processor coupled to the memory. The processor is operative: to receive heterogeneous data from the plurality of decision engines comprising a set of class labels from each of the plurality of decision engines, wherein the set of class labels from at least a first decision engine differs from the set of class labels from at least a second decision engine; to generate a single set of unified class labels from the heterogeneous data; to calculate at least one value corresponding to each of the unified class labels; and to perform decision fusion on the unified class labels and corresponding values to produce the single decision.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

The following drawings are presented by way of example only and without limitation, wherein like reference numerals (when used) indicate corresponding elements throughout the several views, and wherein.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Embodiments of the present invention will be described herein in the context of illustrative methods and apparatus for using a plurality of heterogeneous decision engines to produce a single decision. It is to be appreciated, however, that the invention is not limited to the specific apparatus and/or methods illustratively shown and described herein. Moreover, it will become apparent to those skilled in the art given the teachings herein that numerous modifications can be made to the embodiments shown that are within the scope of the claimed invention. Thus, no limitations with respect to the embodiments shown and described herein are intended or should be inferred.

Figure 1:
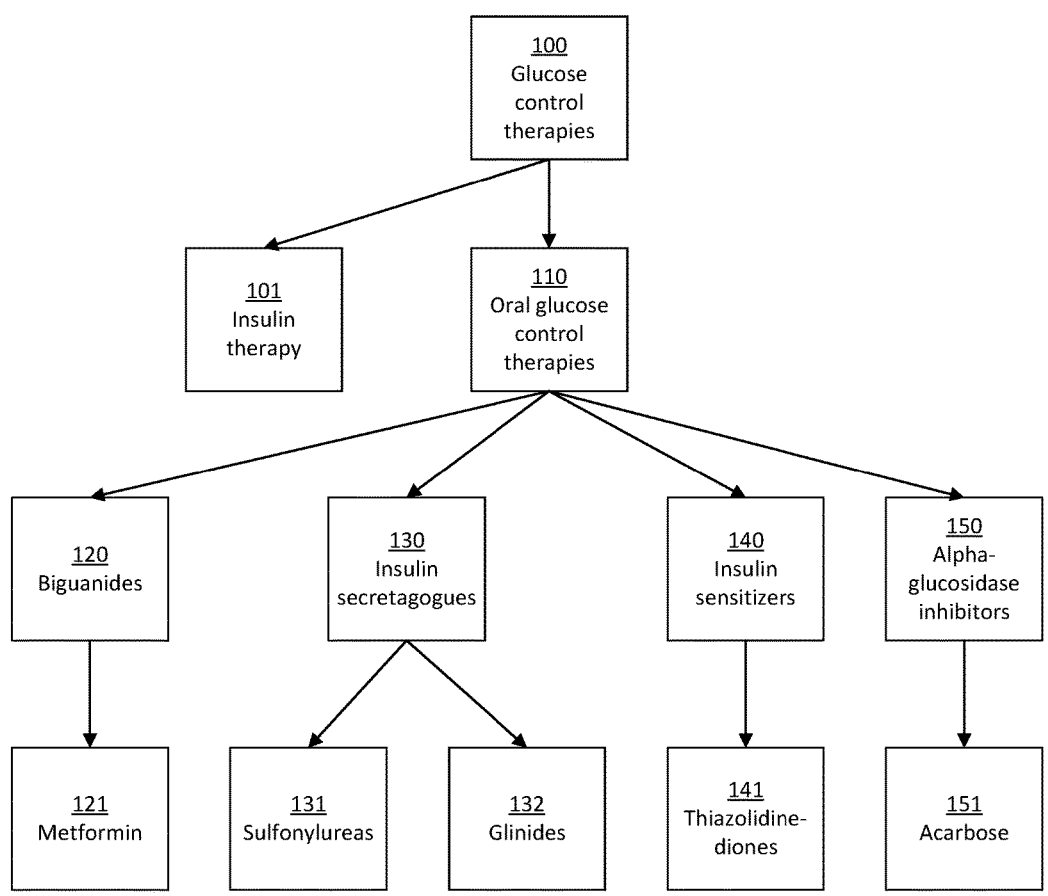
FIG. 1 depicts an exemplary ontology that may be useful in illustrating one or more aspects and/or elements of the invention.

FIG. 1 depicts an exemplary ontology that may be useful in illustrating one or more aspects and/or elements of the invention. FIG. 1 is an ontology of glucose control therapies 100 which include insulin therapy 101 and oral glucose control therapies 110. Oral glucose control therapies 110 include biguanides 120 (such as metformin 121), insulin secretagogues 130 (such as sulfonylureas 131 and glinides 132), insulin sensitizers 140 (such as thiazolidinediones 141), and alpha-glucosidase inhibitors 150 (such as acarbose 151).

Legacy decision engines for determining glucose control therapies for use with a diabetic patient may include a clinical guideline-based decision engine and a patient similarity-oriented decision engine (e.g. using patient cohort analysis). For a given patient, the guideline-based decision engine may recommend sulfonylureas, while the similarity-oriented decision engine may recommend insulin secretagogues. However, as shown on FIG. 1, sulfonylureas 131 are a subclass within (i.e., a type of) insulin secretagogues 130. Thus, in this example, the decision engines are producing outputs having heterogeneous labels with differing granularities: the output of the guideline-based decision engine is labeled using the subclass sulfonylureas 131, while the output of the similarity-oriented decision engine is labeled using the superclass insulin secretagogues 130.

As discussed above, a conventional MCS would be unable to correctly combine the outputs of these two decision engines due to their heterogeneous labels. Illustrative embodiments of the present invention advantageously solve this problem by normalizing heterogeneous decision engine outputs prior to decision fusion. Thus, illustrative embodiments of the present invention advantageously facilitate the use of legacy decision engines within an MCS.

Figure 2:
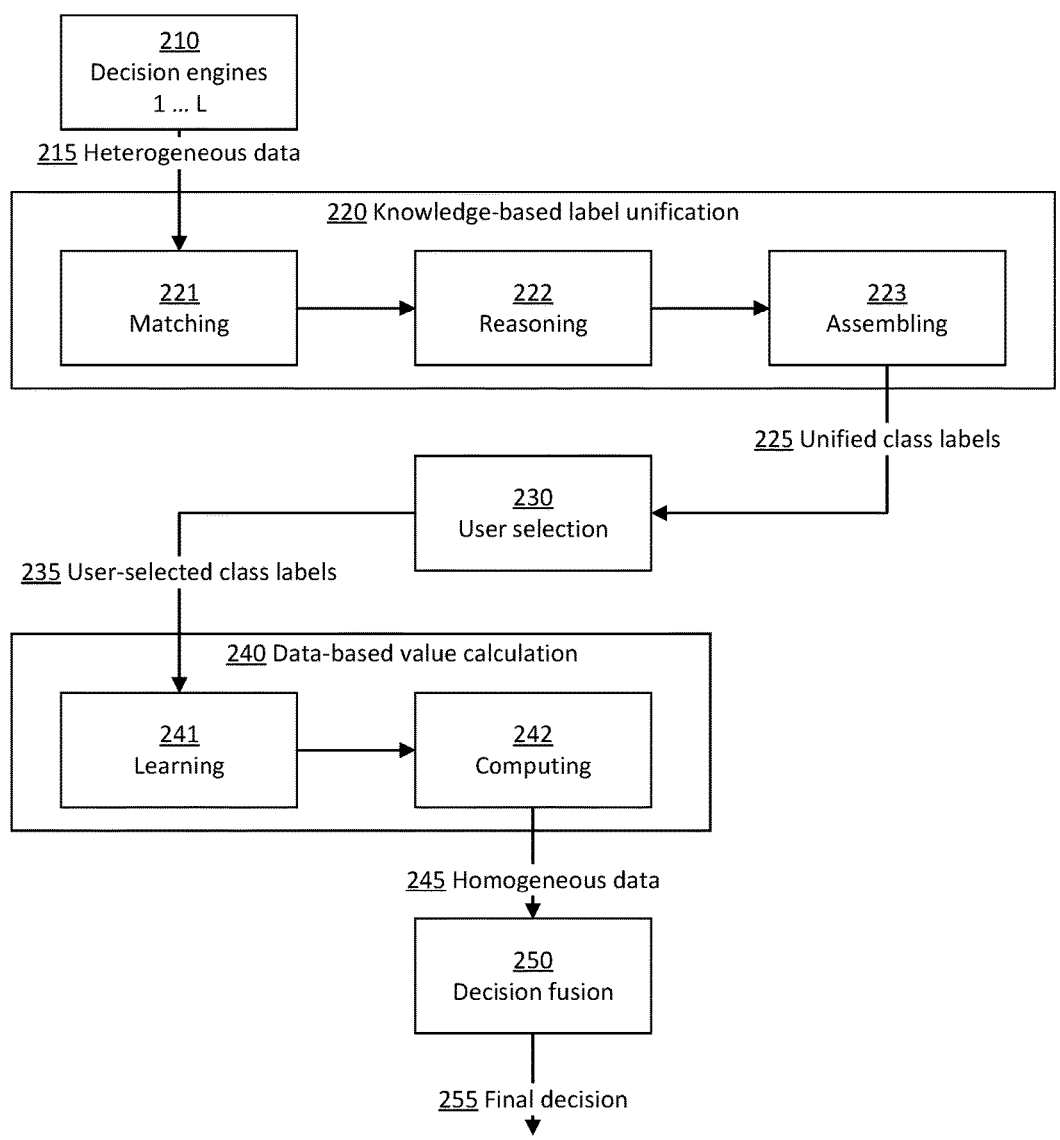
FIG. 2 is a flow diagram depicting at least a portion of an exemplary MCS suitable for use with heterogeneous decision engines, according to an embodiment of the invention.

FIG. 2 is a flow diagram depicting at least a portion of an exemplary MCS suitable for use with heterogeneous decision engines, according to an embodiment of the invention. A plurality of decision engines ($D_1 \ldots D_L$) are collectively shown in FIG. 2 as 210. Each of these decision engines (e.g., $D_i$, where $1 \leq i \leq L$) produces a set of labels (e.g. classes $C_{i,1} \ldots, C_{i,j} \ldots, C_{i,Mi}$, where $1 \leq j \leq M_i$) and corresponding values of the form $P_i(C_{i,j}|x)$ representing the probability that an instance x belongs to class $C_{i,j}$ decided by engine $D_i$.

Different engines $D_i$ may produce different numbers of labels, and hence the value of $M_i$ may be different for different engines. Of course, even where decision engines produce the same number of labels, the labels produced by one engine may differ from the labels produced by another engine. Thus, decision engines may produce different sets of labels, which may be heterogeneous labels with different granularities. In the illustrative embodiment discussed above with reference to FIG. 1, decision engine $D_1$ may be a guideline-based decision engine which generates 4 labels ($M_1=4$) and corresponding probabilities in which classes $C_{1,1}$, $C_{1,2}$, $C_{1,3}$ and $C_{1,4}$ respectively correspond to elements 120, 130, 140 and 150 in FIG. 1, while decision engine $D_2$ may be a patient-oriented decision engine which generates 5 labels ($M_2=5$) and corresponding probabilities in which classes $C_{2,1}$, $C_{2,2}$, $C_{2,3}$, $C_{2,4}$ and $C_{2,5}$ respectively correspond to elements 121, 131, 132, 141 and 151 in FIG. 1. Thus, the plurality of decision engines 210 produce heterogeneous data 215.

In order for this heterogeneous data 215 to undergo conventional decision fusion 250 to produce final decision 255, the heterogeneous data 215 must be normalized to homogeneous data 245. An illustrative normalization process according to embodiments of the claimed invention includes knowledge-based label unification 220, optional user selection 230, and data-based value calculation 240.

Knowledge-based label unification 220 begins with matching 221 which finds same-as relationships between class labels in the heterogeneous data 215. Thus, matching 221 finds class labels generated by different engines (e.g., $D_i$ and $D_{i'}$) which are equivalent such that $C_{i,j}=C_{i',j'}$. For example, matching 221 may find that thiazolidinediones 141 are also known as glitazones, and may thus match class $C_{i,j}$ generated by engine $D_i$ with the label thiazolinediones and class $C_{i',j'}$ generated by engine $D_{i'}$ with the label glitazones. Matching 221 may include string-based and/or ontology-based techniques.

Knowledge-based label unification 220 continues with reasoning 222 which finds subclass relationships between class labels in the heterogeneous data 215. Thus, reasoning 221 searches class labels generated by different engines (e.g., $D_i$ and $D_{i'}$) with different granularities to find the most specified class labels such that $C_{i,j} \subset C_{i',j'}$. For example, reasoning 222 may find that metformin 121 (corresponding to class label $C_{2,1}$ generated by patient-oriented decision engine $D_2$) is a subclass of biguanides 120 (corresponding to class label $C_{1,1}$ generated by guideline-based decision engine $D_1$), while sulfonylureas 131 (corresponding to class label $C_{2,2}$ generated by patient-oriented decision engine $D_2$) and glinides 132 (corresponding to class label $C_{2,3}$ generated by patient-oriented decision engine $D_2$) are both subclasses of insulin secretagogues 130 (corresponding to class label $C_{1,2}$ generated by guideline-based decision engine $D_1$). Reasoning 222 may include structure-based and/or ontology-based techniques.

Knowledge-based label unification 220 concludes with assembling 223 which generates a single unified set of normalized class labels 225. This may be a set of N class labels $\omega_1, \ldots, \omega_N$ such that, each class label $\omega_k$ ($1 \leq k \leq N$) is either equivalent to a class label generated by at least one of the decision engines ($\omega_k = C_{i,j}$) as determined by matching 221 and/or is a subclass of a class label generated by at least one of the decision engines ($\omega_k \subset C_{i,j}$) as determined by reasoning 222.

After knowledge-based label unification 220, the resulting set of unified class labels 225 may then be presented to the user in step 230 to allow the user to select a subset of one or more classes 235 to be used for data-based value calculation 240. Such user selection is optional: if the user does not select any of the classes (or if the user selects all of the classes), then by default, the full set of unified class labels 225 will be considered to be the user-selected subset 235 and used for the data-based value calculation. Thus, the user selection 230 is a flexible way to decide which class labels need to be finally calculated for their fusion values.

After the user selection 230, the exemplary normalization process continues with data-based value calculation 240, which begins with learning 241 which assigns a weight for each of the user-selected subset 235 or, if there is no user selection 230, for each of the unified class labels 225. These weights are preferably assigned based on training from real data, including the probability values generated by decision engines 210. Besides these data-driven weights, knowledge-driven weights may also be considered.

In some embodiments, learning 241 may include a logistic regression model, in which the probability of a particular outcome is transformed to the linear predictor function using a log it function (the natural logarithm of the odds):

$$logit(\pi_i) = \log\left(\frac{\pi_i}{1-\pi_i}\right) = \beta_0 + \beta_1 x_i.$$

An example is dichotomous exposure, with an "outcome" referring to whether a class label is the final decision. If yes, then it's an exposed outcome, else it's an unexposed outcome: i.e., exposed=1 and unexposed=0. The probability of a class label given exposure log $it(\pi_{D|E})=\beta_0+\beta_1$. The probability of a class label given non-exposure log $it(\pi_{D|E^c})=\beta_0$. Thus, the odds ratios are:

$$logit(\pi_{D|E}) - logit(\pi_{D|E^c}) = \beta_0 + \beta_1 - \beta_0$$

$$\log\left(\frac{\pi_{D|E}}{1-\pi_{D|E}}\right) - \log\left(\frac{\pi_{D|E^c}}{1-\pi_{D|E^c}}\right) = \log\left(\frac{\pi_{D|E}}{1-\pi_{D|E}} \Big/ \frac{\pi_{D|E^c}}{1-\pi_{D|E^c}}\right) = \beta_1$$

$$OR = \exp(\beta_1)$$

A log-likelihood can then be calculated as $l(\beta) = \log L(\beta)$ where $$l = \sum_{i=1}^{n}\left[Y_i \log\left(\frac{\exp(x_i'\beta)}{1+\exp(x_i'\beta)}\right) + (1-Y_i)\log\left(1-\frac{\exp(x_i'\beta)}{1+\exp(x_i'\beta)}\right)\right].$$

An iterative optimization process can then be performed using the objective function $$\hat{\beta} = \underset{\beta}{\operatorname{argmin}} J(\beta),$$

where $J(\beta)=-l(\beta)$ and a gradient descent repeated until convergence:

$$\beta_j \leftarrow \beta_j - \alpha \frac{\partial J(\beta)}{\partial \beta_j}$$

$$\frac{\partial J(\beta)}{\partial \beta_j} = \sum_{i=1}^{N} x_{i,j}\left(Y_i - \frac{1}{1+e^{-\beta \cdot X_i}}\right)$$

where $\alpha$ is the learning rate.

Data-based value calculation 240 concludes with computing 242 which generates a value for each of the unified class labels for instance x. These values are preferably computed for each decision engine to facilitate subsequent decision fusion:

$$d_{i,j}(x) = \sum_{l=1}^{k_j} P_i(C_{il} | x) \times w_{lj}$$

where $w_{lj}$ is the weight as learned, and $P_i(C_{il}|x)$ is the probability of an instance x belonging to class $C_{il}$ decided by engine $D_i$. The result of data-based value calculation is homogeneous data in the form of a matrix of values corresponding to the normalized class labels:

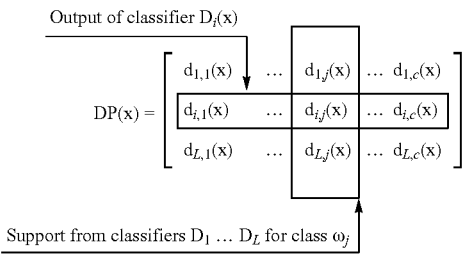

This homogeneous data 245 can then be input using conventional decision fusion 250 to produce a final decision 255.

Given the discussion thus far, it will be appreciated that, in general terms, an exemplary method for using a plurality of decision engines to produce a single decision according to an aspect of the invention comprises: receiving heterogeneous data from the plurality of decision engines comprising a set of class labels from each of the plurality of decision engines, wherein the set of class labels from at least a first decision engine differs from the set of class labels from at least a second decision engine; generating a single set of unified class labels from the heterogeneous data; calculating at least one value corresponding to each of the unified class labels; and performing decision fusion on the unified class labels and corresponding values to produce the single decision.

Exemplary System and Article of Manufacture Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

Figure 3:
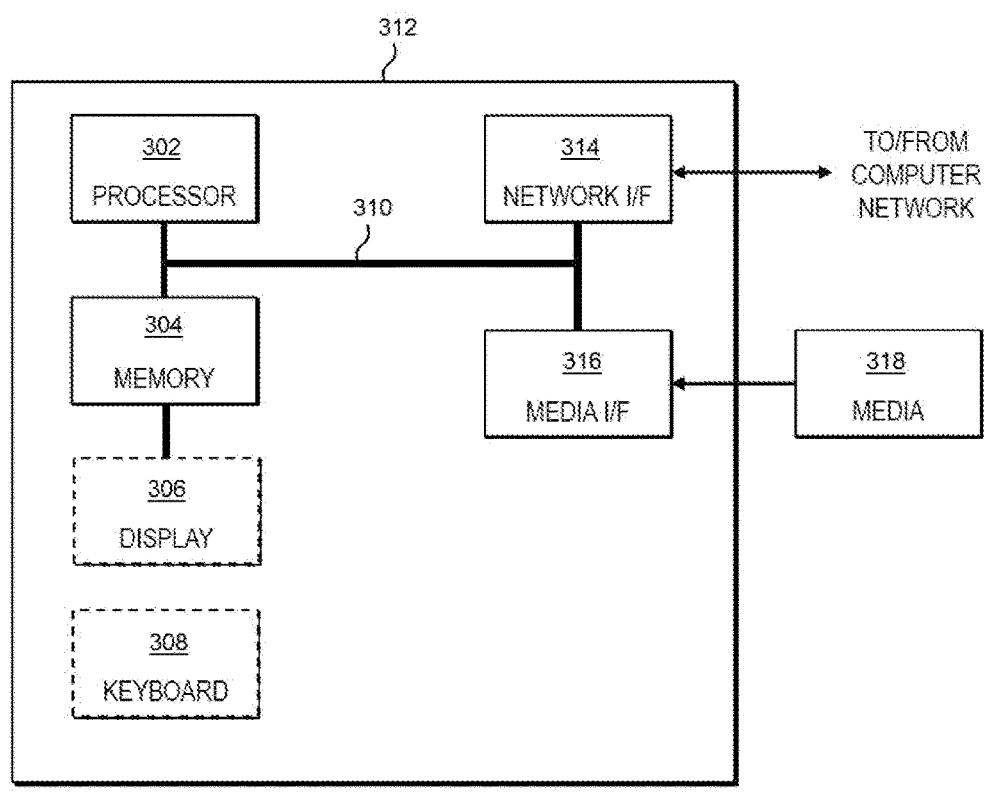
FIG. 3 depicts a computer system that may be useful in implementing one or more aspects and/or elements of the invention.

One or more embodiments can make use of software running on a general purpose computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 418 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, a knowledge-based label unification module, and a data-based value calculation module. The method steps can then be carried out using the distinct software modules and/or sub-modules of the system, as described above, executing on one or more hardware processors 302. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for using a plurality of decision engines to produce a single decision, the method comprising:
   receiving heterogeneous data from the plurality of decision engines, each of the decision engines implemented with a hardware processor, comprising a set of class labels from each of the plurality of decision engines, wherein the set of class labels from at least a first decision engine differs from the set of class labels from at least a second decision engine;
   generating a single set of unified class labels from the heterogeneous data;
   calculating at least one value corresponding to each of at least a subset of the unified class labels; and
   performing decision fusion on at least the subset of the unified class labels and corresponding values to produce the single decision.

2. The method of claim 1, wherein generating a single set of unified set of unified class labels comprises knowledge-based label unification and wherein calculating at least one corresponding value comprises data-based value calculation.

3. The method of claim 1, wherein generating a single set of unified class labels from the heterogeneous data comprises:
   finding equivalent class labels within the heterogeneous data;
   finding most-specified class labels within the heterogeneous data; and
   generating the single set of unified class labels from the equivalent class labels and the most-specified class labels.

4. The method of claim 3, wherein finding equivalent class labels within the heterogeneous data comprises at least one of string-based matching and ontology-based matching.

5. The method of claim 3, wherein finding most-specified class labels within the heterogeneous data comprises at least one of structure-based reasoning and ontology-based reasoning.

6. The method of claim 1, wherein calculating at least one value corresponding to each of at least a subset of the unified class labels comprises:
   presenting the set of unified class labels to a user; and
   obtaining selection by the user of the subset of the unified class labels.

7. The method of claim 6, wherein calculating at least one value corresponding to each of at least a subset of the unified class labels further comprises calculating the at least one value corresponding to each of only the subset of the unified class labels.

8. The method of claim 1, wherein calculating at least one value corresponding to each of at least a subset of the unified class labels comprises calculating the at least one value corresponding to each of the set of unified class labels.

9. The method of claim 1, wherein calculating at least one value corresponding to each of at least a subset of the unified class labels comprises:
   assigning at least one weight to each of at least the subset of the unified class labels; and
   calculating the at least one value corresponding to each of at least the subset of the unified class labels based at least in part on the at least one weight assigned to each of at least the subset of the unified class labels.

10. The method of claim 9, wherein assigning at least one weight to each of at least the subset of the unified class labels comprises applying an iterative optimization process to a logistic regression model.

11. The method of claim 9, wherein assigning at least one weight to each of at least the subset of the unified class labels comprises considering at least one data-driven weight and at least one knowledge-driven weight.

12. The method of claim 1, wherein the at least one value corresponding to each of the unified class labels comprises a plurality of values corresponding to respective ones of the plurality of decision engines.

13. An apparatus, comprising:
   a memory; and
   at least one processor coupled with the memory and operative:
      to receive heterogeneous data from a plurality of decision engines comprising a set of class labels from each of the plurality of decision engines, wherein the set of class labels from at least a first decision engine differs from the set of class labels from at least a second decision engine;
      to generate a single set of unified class labels from the heterogeneous data;
      to calculate at least one value corresponding to each of the unified class labels; and
      to perform decision fusion on the unified class labels and corresponding values to produce a single decision.

14. The apparatus of claim 13, wherein generating a single set of unified set of unified class labels comprises knowledge-based label unification and wherein calculating at least one corresponding value comprises data-based value calculation.

15. The apparatus of claim 13, wherein generating a single set of unified class labels from the heterogeneous data comprises:
   finding equivalent class labels within the heterogeneous data;
   finding most-specified class labels within the heterogeneous data; and
   generating the single set of unified class labels from the equivalent class labels and the most-specified class labels.

16. The apparatus of claim 15, wherein finding equivalent class labels within the heterogeneous data comprises at least one of string-based matching and ontology-based matching, and wherein finding most-specified class labels within the heterogeneous data comprises at least one of structure-based reasoning and ontology-based reasoning.

17. The apparatus of claim 13, wherein calculating at least one value corresponding to each of at least a subset of the unified class labels comprises:
   presenting the set of unified class labels to a user; and
   obtaining selection by the user of the subset of the unified class labels.

18. The apparatus of claim 17, wherein calculating at least one value corresponding to each of at least a subset of the unified class labels further comprises calculating the at least one value corresponding to each of only the subset of the unified class labels.

19. The apparatus of claim 17, wherein calculating at least one value corresponding to each of at least a subset of the unified class labels comprises calculating the at least one value corresponding to each of the set of unified class labels.

20. A computer program product comprising a non-transitory machine-readable storage medium having machine-readable program code embodied therewith, said machine-readable program code comprising:
   machine-readable program code configured:
      to receive heterogeneous data from a plurality of decision engines comprising a set of class labels from each of the plurality of decision engines, wherein the set of class labels from at least a first decision engine differs from the set of class labels from at least a second decision engine;
      to generate a single set of unified class labels from the heterogeneous data;
      to calculate at least one value corresponding to each of the unified class labels; and
      to perform decision fusion on the unified class labels and corresponding values to produce a single decision.

* * * * *